United States Patent

Westphal et al.

[11] Patent Number: 5,746,575
[45] Date of Patent: May 5, 1998

[54] BLOOD PUMP AS CENTRIFUGAL PUMP

[75] Inventors: Dieter Westphal, Woerthsee; Helmut Reul, Dueren; Guenter Rau, Aachen, all of Germany

[73] Assignee: Baxter International, Inc., Deerfield, Ill.

[21] Appl. No.: 569,098
[22] PCT Filed: Jun. 23, 1994
[86] PCT No.: PCT/EP94/02049
§ 371 Date: Dec. 22, 1995
§ 102(e) Date: Dec. 22, 1995
[87] PCT Pub. No.: WO95/00185
PCT Pub. Date: Jan. 5, 1995

[30] Foreign Application Priority Data

Jun. 25, 1993 [DE] Germany ............ 43 21 260.3

[51] Int. Cl.$^6$ .................................... F04D 29/04
[52] U.S. Cl. .................................... 415/206; 415/900
[58] Field of Search .................... 415/206, 900; 417/423.12, 424.1

[56] References Cited

U.S. PATENT DOCUMENTS

| | | | |
|---|---|---|---|
| 4,984,972 | 1/1991 | Clausen et al. | 415/900 |
| 5,147,187 | 9/1992 | Ito et al. | 415/900 |
| 5,322,413 | 6/1994 | Vescovini et al. | 415/206 |
| 5,360,317 | 11/1994 | Clausen et al. | 415/206 |
| 5,399,074 | 3/1995 | Nose et al. | 417/423.12 |
| 5,458,459 | 10/1995 | Hubbard et al. | 415/206 |

*Primary Examiner*—John T. Kwon
*Attorney, Agent, or Firm*—Diller, Ramik & Wight, PC

[57] ABSTRACT

In a pump housing (10), the blood pump comprises an impeller (13) with a flat plate (30) and blades (34) projecting therefrom. The impeller (13) is supported between balls (18,20) forming an axial sliding bearing. The front wall (35) and the back wall (14) of the pump housing extend substantially parallel to the plate (30) of the impeller (13). The height of the blades (34) linearly decreases with increasing radius so that the gap between the front wall (35) and the blades (34) increases outwards. Since the circumferential speed increases as well, the shearing rate remains constant. Between the plate (30) of the impeller and the back wall (14), a gap of constant width is provided, in which secondary flows are produced, thereby avoiding dead water zones.

12 Claims, 3 Drawing Sheets

BLOOD PUMP AS CENTRIFUGAL PUMP

BACKGROUND OF THE INVENTION

The invention relates to a blood pump which is configured as a centrifugal pump, comprising an impeller rotating in a pump housing.

A blood pump from which the precharacterizing part of claim 1 starts is known from U.S. Pat. No. 4,507,048. This blood pump comprises an impeller being supported in the pump housing between two tip bearings, the blades of the impeller being arranged at the front of a central cone. On the back side of the central cone, there is a plate having a constant distance from the back wall of the pump housing. The profiling of the blades is similar to that of aircraft wings, and they have an angle of contact of about 150. The blades are covered by a cone envelope in which another cone envelope is arranged so that the impeller forms an altogether rotating partially hollow body wherein the blades are arranged.

From EP 0 451 376 A1, a blood pump is known wherein the impeller comprises a plane plate from which the blades project to the front, towards the inlet. The blades are slightly bent and their height decreases linearly outward. The impeller is attached to a shaft one end of which is supported in an extension of the pump housing. The front wall of the pump housing has a truncated configuration, and, with increasing radius, the back wall is set back.

Further, a blood pump is known from U.S. Pat. No. 4,589,822, wherein the impeller is fastened to a shaft which is also supported outside the pump housing. The impeller comprises linear blades whose height decreases linearly outwards. The front wall of the pump housing has a truncated configuration and, with the radius increasing, the back wall is set back. The blades only have an angle of contact of about 60°. Outwards, they project beyond the plate.

From U.S. Pat. No. 4,984,972, a blood pump is known in which an impeller consisting of a plate with a plane upper surface and a conically extending lower surface is oscillatingly supported on a tip bearing. The height of the blades of the impeller linearly decreases radially outward, the blades terminating at the outer plate edge.

Centrifugal pumps for industrial applications are configured such that they have a high pump rate with low delivery pressure. On the contrary, blood pumps have to be configured for low pump rates and relatively high pressures. A problem with blood pumps is that they are subject to considerably varying operational conditions and that it has to be ensured that harm to blood is avoided. A blood pump, for example, is used for taking over the pump function of the heart of a patient during an operation. When a vasodilative medicine is administered to the patient, the fluid resistance of the patient body decreases and the pressure against which the blood pump has to feed decreases. Further, blood pumps can be used for fully taking over the heart function or for exerting a heart-supporting function only. Accordingly, a blood pump has to be capable of delivering varying quantities (by means of different speeds). Furthermore, a blood pump has to be configured such that it operates in the occurring wide application ranges with minimum blood disintegration. Blood disintegration happens, e.g., by local temperature rises of the blood pump in the support region of the impeller, but particularly by transverse stresses and shearing stresses to which the blood is exposed in the centrifugal pump. Such effects cause a disintegration of the blood due to hemolysis, thrombocytes being activated and aggregating. This may lead to perilous clot formations. Clot formations also form in dead water zones where the pump housing is insufficiently flown through.

An optimization of the flow conditions in blood pumps with the target to avoid any harm to blood cannot be achieved at present on the basis of calculations and theoretical considerations due to the various operational conditions a blood pump may be exposed to. When designing a blood pump, the engineer is dependent, to a great extent, on empiric research.

SUMMARY OF THE INVENTION

It is the object of the invention to provide a blood pump which operates with minimum blood disintegration and which has a simple construction so that it can be manufactured as a one-way article at low cost.

In the blood pump according to the invention, the impeller is supported between axial sliding bearings within the pump housing, whereby complex rolling bearings and shaft seals are omitted. Thereby, friction is held on a low level so that a frictional heating is practically unnoticeable. The term axial sliding bearings includes tip bearings and also particularly a thrust ball bearing with a ball arranged along the rotational axis. The impeller comprises blades which freely project from a plate and are not encompassed by a cover. The individual blades have a very high angle of contact of 90°–120°, preferably of about 110°. Due to the high angle of contact, the blood pump is capable of delivering the required high pressure and, on the other hand, of performing the increase in pressure continuously and with low transverse stresses.

With the radius increasing, the height of the blades decreases linearly outwards, while the front wall of the pump housing extends substantially parallel to the plate of the impeller but has a small conicity of about 3° to 10°, so that air bubbles can escape to the inlet when the pump stands in a vertical position. Thereby, the distance of the blades from the front wall of the housing increases linearly so that the gap formed between the blades and the front wall of the housing linearly increases with the radius. Since the circumferential speed also increases with the radius, the shearing rate at the front side of the impeller is substantially constant. This means that the normally appearing shearing stress peaks are avoided. The gap formed between the plate and the back wall of the pump housing is constant at the back side of the plate. The gap width should be greater than 1 mm, preferably about 2 mm. Thereby, secondary flows are produced at the back side of the impeller, in which the blood continuously circulates so that the formation of dead water zones is not possible.

The blades begin only relatively far at the outside on the impeller, i.e. the blade-free central region has a relatively large diameter with respect to the outer diameter of the impeller. The blade inlet angle only amounts to 18°–25°. This small inlet angle prevents shearing stress peaks in the very critical inlet area. The blade outlet angle is also much smaller than is common in centrifugal pumps of this size.

Hereinafter, an embodiment of the invention is described in detail with reference to the drawings, in which:

DESCRIPTION OF THE REFERRED EMBODIMENTS

Figure 1:
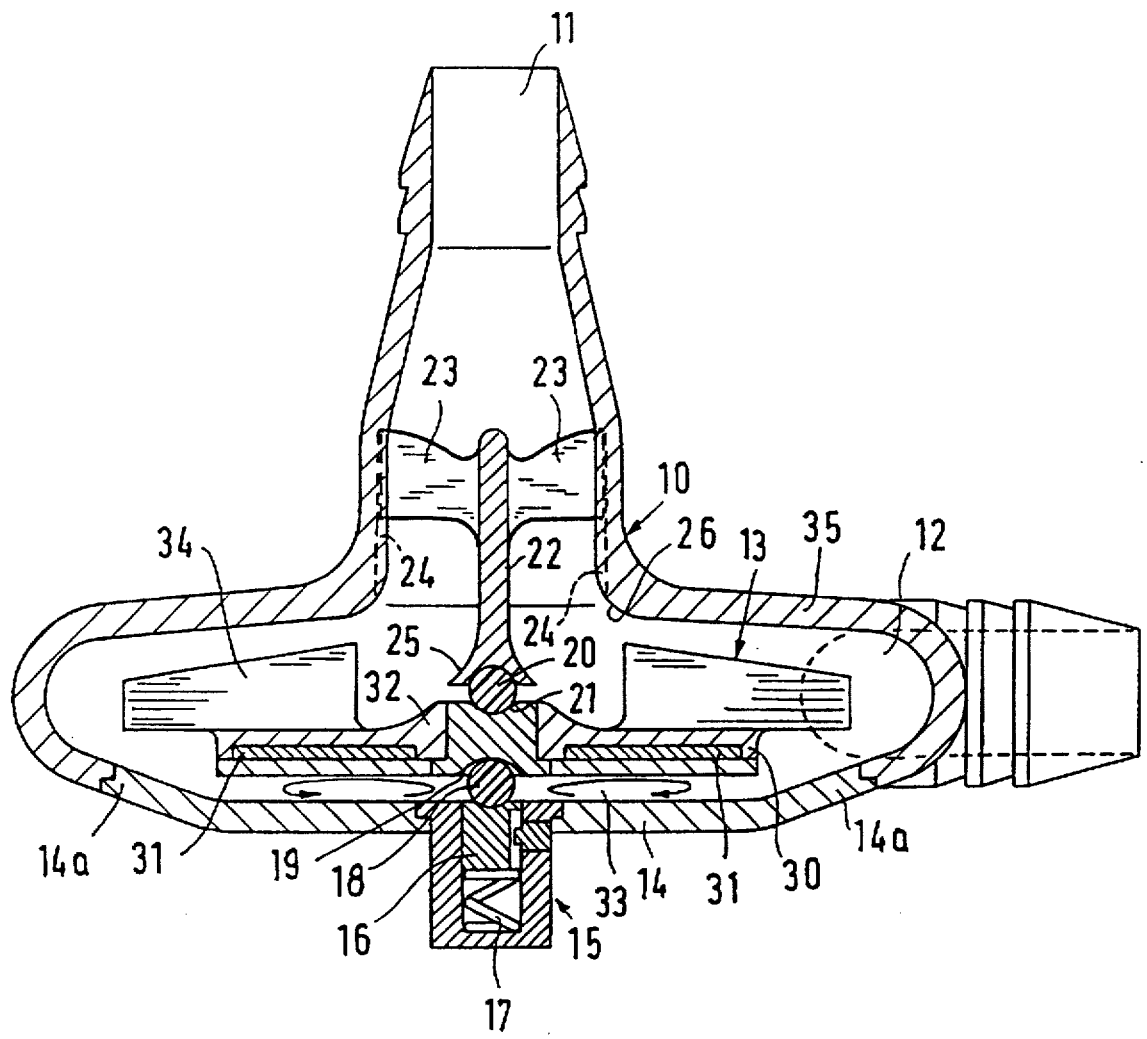
FIG. 1 shows a longitudinal section through the blood pump.

The blood pump comprises a round flat (plate-shaped) pump housing 10 having a diameter of about 60 mm which is provided with an inlet 11 along its axis. The outlet 12 is tangentially arranged on the periphery of the pump housing 10.

In the pump housing 10, the impeller 13 is supported by means of an axial sliding bearing. In the back wall 14 of the pump housing, there is a supporting device 15 for a ball holder 16. The supporting device 15 includes a spring 17 which presses the ball holder 16 against the impeller 13. Along the axis of the impeller, a ceramic ball 18 is adhered to the ball holder 16. This ball 18 projects into a ball cup 19 of the impeller 13, the diameter of the ball cup 19 being generally twice as large as the diameter of the ball 18.

Another ceramic ball 20 arranged on the impeller axis and immerging into a ball cup 21 which is opposed to the ball cup 19 serves as abutment for the ball 18. The ball 20 is adhered to a ball holder 22 which projects into the tubular inlet 11 and is provided with laterally projecting ribs 23 protruding into longitudinal grooves 24 of the tubular wall of the inlet 11. In the two spherical thrust bearings, the ratio $R_{spherical\ cap}/R_{ball}$ is between 1.5/1 and 3/1 so that the ball has only punctual contact with the associated spherical cap. Ball and spherical cap consist of a material combination providing favorable friction conditions, e.g. steel—ceramic or ceramic—ceramic.

The free end 25 of the ball holder 22 is expanded in a trumpet-like manner, the expansion having a radius of about 5 mm. This expansion serves to radially deviate the blood coming from the inlet 11 to the impeller. The transition 26 from the inlet 11 to the pump room of the pump housing has a radius of curvature of about 3 mm. The transition from the axial flow in the inlet 11 to the rotational flow in the pump room is made without any abrupt change of cross section. The inlet region of the impeller, which is strongly influenced by the flow deviation by 90°, is particularly favorable to flow and configured so as to treat the blood carefully. This is achieved by the fact that at the transition of the inlet 11 to the pump room, the flow cross section increases by about the factor 6 (from 140 mm² in the inlet connection piece to 850 mm² at the blade beginning), and that, on the other hand, the deviation radii are particularly large there.

The impeller 13 comprises a plane plate 30 in which ferromagnetic plates 31 are embedded. In its central portion 32 at the side facing the inlet 11, the plate 30 is configured so as to be thickened by less than the plate thickness. This thickening in the central portion 32 is rounded, the radius corresponding to that of the trumpet-shaped region 25. The central portion 32 is free of blades. Its radius R1 is 9 mm and is slightly larger than the radius of the inlet 11 at the transition into the pump chamber. The radius R2 of the impeller is 24 mm and the radius R3 of the plate 30 is 18 mm.

A gap 33 of constant width of about 2 mm is formed between the back side of the plate 30 and the back wall 14. Upon rotation of the impeller 13, secondary flows, as indicated by the arrows, are formed in the gap 33. These secondary flows prevent the formation of dead water zones in the gap 33.

The impeller 13 comprises four to seven (here: five) blades 34 which begin at the periphery of the central portion 32 and radially project beyond the plate 30 by about one third of the blade length. In the region of the projecting lengths of the blades 34, the back wall 14 is provided with a sloping 14a in order to compensate for the lack of plate 30 in the outer region of the pump chamber. Thus, the width of the pump chamber reduces towards the outer edge and towards outlet 12.

The front wall 35 of the pump chamber extends approximately parallel to the central portion of the back wall 14 and the plate 30. The blades 34 have their greatest height at the inner end, i.e. at the periphery of the central portion 32. The blade height decreases linearly outwards to about half. The gap between the front wall 35 of the pump housing and the blade edges widens radially outwards. Since the circumferential speed of the blood also increases radially outwards, the shearing rate remains constant.

Figure 2:
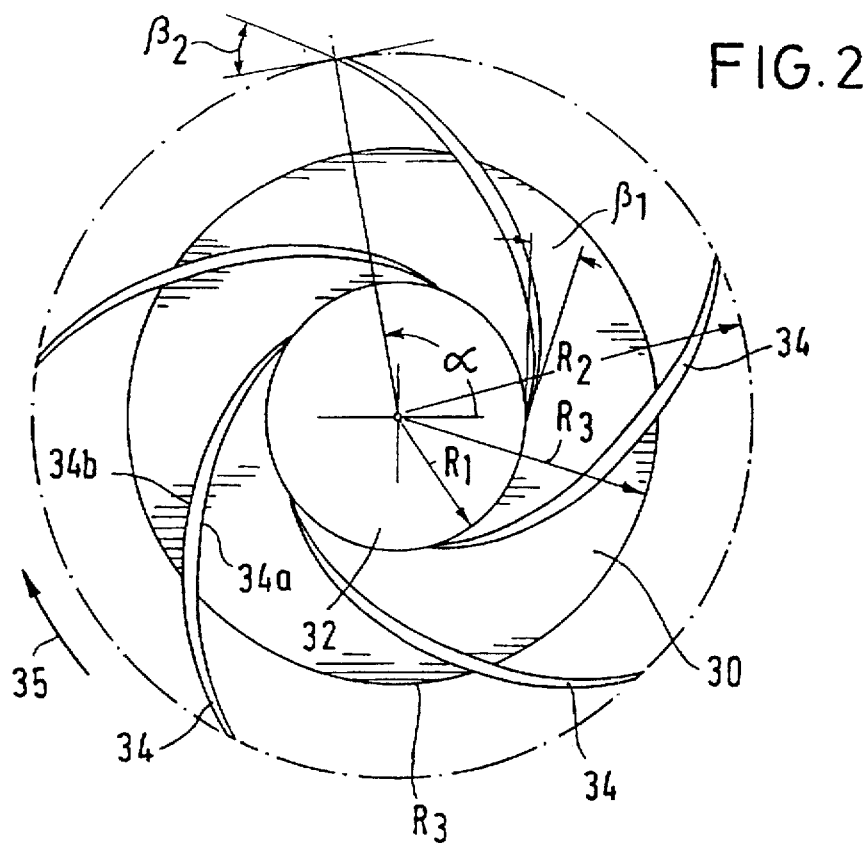
FIG. 2 shows a view of the impeller.

As shown in FIG. 2, each blade 34 is curved in an arc-like manner in the rotational direction 35, the angle of contact α of one blade being 100°. The blade inlet angle β1, namely the tangent angle of the blade to the central portion 32, amounts to 20° and the blade outlet angle β2, namely the tangent angle of the blade to the circle having the radius R2 and encompassing the blade ends, amounts to 30°. The concave inner side 34a of the blade forms the suction side and the convex outer side 34b forms the pressure side. The blades have their smallest thickness at the inlet end and the outlet end. For reasons of stability, the blade thickness increases towards the center, the blade having the greatest thickness in the central portion. The blade is rounded at the inlet end.

Figure 3:
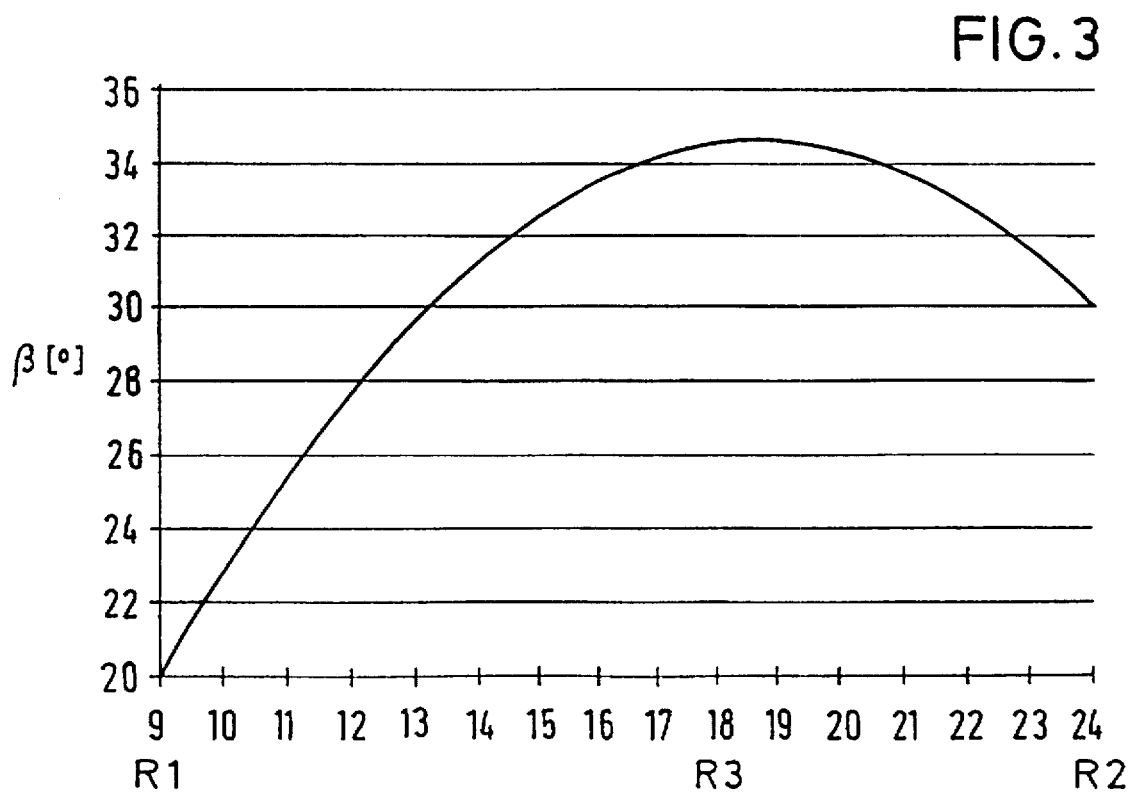
FIG. 3 shows the course of the blade angle β as a function of the radius r.

FIG. 3 shows the course of the tangent angle β of the blade as a function of the radius r. The course β(r) corresponds to a polynomial of the second degree:

$$\beta(r)=Ar^2+Br+C.$$

A, B, and C are constants. In the present embodiment, A=−0.16; B=5.95; C=−20.56.

The described structural shape of pump housing and impeller permits an essentially smaller filling volume than is the case with other blood pumps of the same capacity. The filling volume here only amounts to 30 ml (milliliters). Owing to the small filling volume, the extracorporeal blood volume is reduced and the contact of the blood with foreign surfaces, which considerably contributes to harming the blood, is reduced. The blood pump can be manufactured of a small number of parts at low cost. For medical reasons, it is provided for being used only once.

Figure 4:
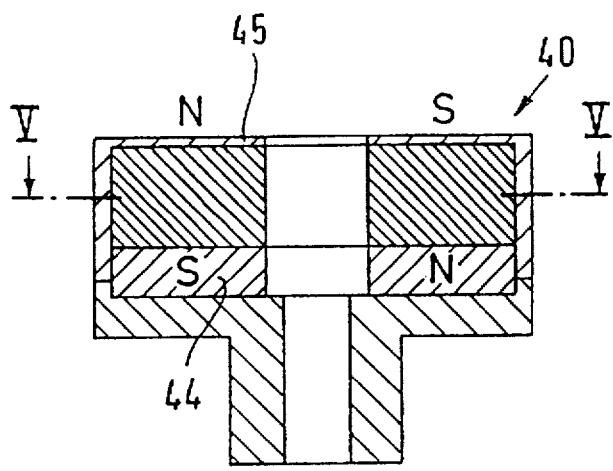
FIG. 4 shows a longitudinal section through the driving wheel.
Figure 5:
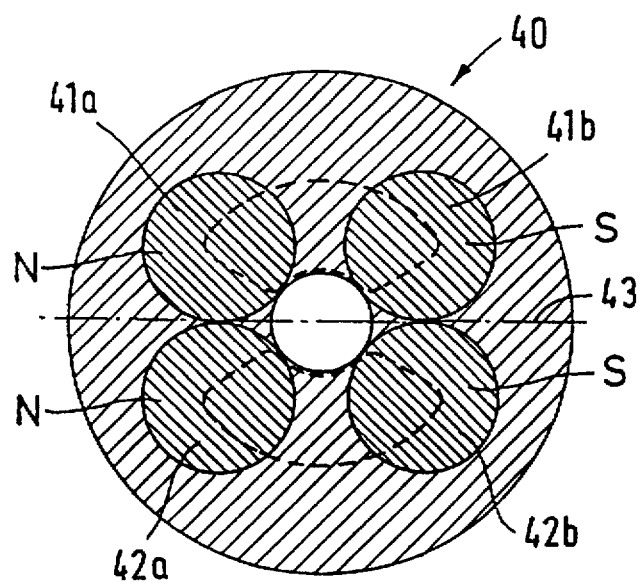
FIG. 5 shows a section along line V—V—of FIG. 4.
Figure 6:
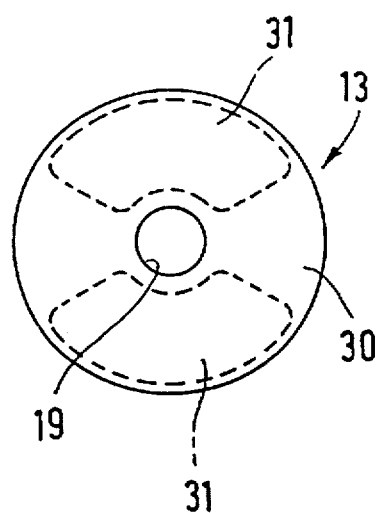
FIG. 6 shows the arrangement of the soft magnetic plates in the impeller.

The described blood pump is used in combination with the driving wheel 40 illustrated in FIGS. 4 and 5. This driving wheel comprises two pairs of bar magnets 41a, 41b;42a,42b, each pair being arranged on a different side of the radius 43 of the driving wheel. In the drawings, the polarities of the bar magnets are indicated with N (north pole) and S (south pole). The back sides of the bar magnets are in contact with a ferromagnetic plate 44 which forms the pole backflow path. The front side 45 of the bar magnets has a magnetic effect on the ferromagnetic plates 31 through the wall of the pump housing 10, said plates closing the magnetic flux on the front side of the bar magnets. The driving wheel 40 is driven by a motor and thus pulls along the disc 30 supported in the pump housing 10. The plates 31 included in the disc 30 only consist of soft magnetic (ferromagnetic) material, e.g. of simple constructional steel. Each of them has a circumferential extension of 120° and a thickness of 1 mm.

When the pump is driven with a speed of 3,000 rpm, it delivers a quantity of 4 l/min (liters per minute) with a delivery pressure of 180 mmHg.

Although a preferred embodiment of the invention has been specifically illustrated and described herein, it is to be understood that minor variations may be made in the apparatus without departing from the spirit and scope of the invention, as defined the appended claims.

We claim:

1. A pump comprising a pump housing having an axial inlet;

a tangential outlet;

a front wall;

a back wall;

an impeller rotatably supported in said pump housing, said impeller comprising a plate having a back side arranged at a substantially constant distance from the back wall of said pump housing, blades projecting from the plate and beyond the plate in a radially outward direction, said blades having a height that decreases in the radially outward direction;

wherein the front wall of said pump housing extends substantially parallel to the plate of said impeller and the back wall of said pump housing includes a circumferential sloping portion located beyond the plate and defining a transition to the tangential outlet.

2. The pump according to claim 1 wherein the plate has a central portion which is thickened by less than the plate thickness at a side facing said inlet, and said blades begin adjacent to said central portion.

3. The pump according to claim 2 wherein each blade has a blade inlet angle ($\beta 1$) defined as the tangent angle of each blade to said central portion of said plate ranging substantially between 18°–25°.

4. The pump according to claim 1, wherein each blade extends over a circumferential angle of contact of 90° to 120°.

5. The pump according to claim 1 wherein each blade has a blade outlet angle ($\beta 2$) defined as the tangent angle of each blade to a circle encompassing blade ends ranging substantially between 25°–40°.

6. The pump according to claim 1 wherein the plate includes a central portion and the ratio of R1/R2 between the radius R1 of said central portion of said plate which is free of blades and the radius R2 of a circle encompassing blade ends is 0.25–0.5.

7. The pump according to claim 1, wherein the thickness of each blade increases towards a central portion of each blade so that each blade has its greatest thickness in its central portion.

8. The pump according to claim 1, wherein a blade angle $\beta$, defined as the tangent angle of the median line of each blade, corresponds to a polynomial of the second degree $Ar^2+Br+C$, wherein r is the radius and A, B, and C are constants.

9. The pump according to claim 1 wherein said impeller further includes two magnetic plates and a driving wheel which includes two pairs of bar magnets, each of which is arranged on a different side of the diameter of said driving wheel.

10. The pump of claim 1 wherein the impeller is supported by means of axial sliding bearings.

11. The pump according to claim 10 wherein the axial sliding bearings each comprise a ball which engages into a ball cup of said plate, and the diameter of each ball cup being larger than that of each said ball.

12. The pump of claim 10 wherein means of axial sliding bearings includes two spherical thrust bearings.

* * * * *